United States Patent [19]

Anderson

[11] 4,249,524
[45] Feb. 10, 1981

[54] KNEE STABILIZER

[76] Inventor: George C. Anderson, 2883 Doidge Ave., Pinole, Calif. 94564

[21] Appl. No.: 124,862

[22] Filed: Feb. 26, 1980

Related U.S. Application Data

[63] Continuation of Ser. No. 919,870, Jun. 28, 1978, abandoned.

[51] Int. Cl.³ .............................................. A61F 3/00
[52] U.S. Cl. ..................................... 128/80 C; 128/88
[58] Field of Search .................... 128/80 C, 80 F, 88, 128/165; 2/22, 24

[56] References Cited

U.S. PATENT DOCUMENTS

| 58,403 | 10/1886 | Goodwin | 128/88 |
|---|---|---|---|
| 901,592 | 10/1908 | Clegg | 128/88 X |
| 1,295,297 | 2/1919 | French | 128/88 X |
| 1,374,177 | 4/1921 | Barry | 128/88 |
| 2,460,895 | 2/1949 | Meany | 128/80 C |
| 2,467,907 | 4/1949 | Peckhan | 128/88 |
| 3,194,233 | 7/1965 | Peckham | 128/80 C |
| 3,350,719 | 11/1967 | McClure | 2/22 |
| 3,581,741 | 6/1971 | Rosman, et al. | 128/80 C |
| 3,885,252 | 5/1975 | Nakajima | 128/80 F |
| 4,097,932 | 7/1978 | Lacey | 128/80 F X |

Primary Examiner—John D. Yasko
Attorney, Agent, or Firm—Harry A. Pacini

[57] ABSTRACT

A knee stabilizer that allows complete freedom of movement of the leg and knee for support and protection of a knee joint, primarily to the medial collateral ligament or lateral collateral ligament of the knee comprising a double hinged single side brace having a rigid support bar formed to be positioned away from the knee aside the knee joint said, support pivotally hinged at one end to an upper padded plate and at the other end pivotally hinged to a lower padded plate; the upper padded plate removably secured to the thigh and the lower padded plate removably secured to the lower leg or calf.

7 Claims, 3 Drawing Figures

U.S. Patent     Feb. 10, 1981     4,249,524
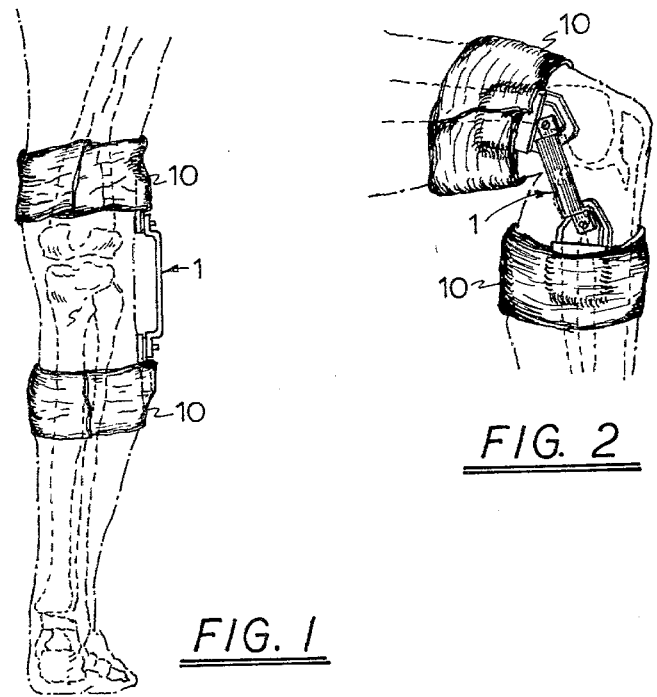
FIG. 1
FIG. 2
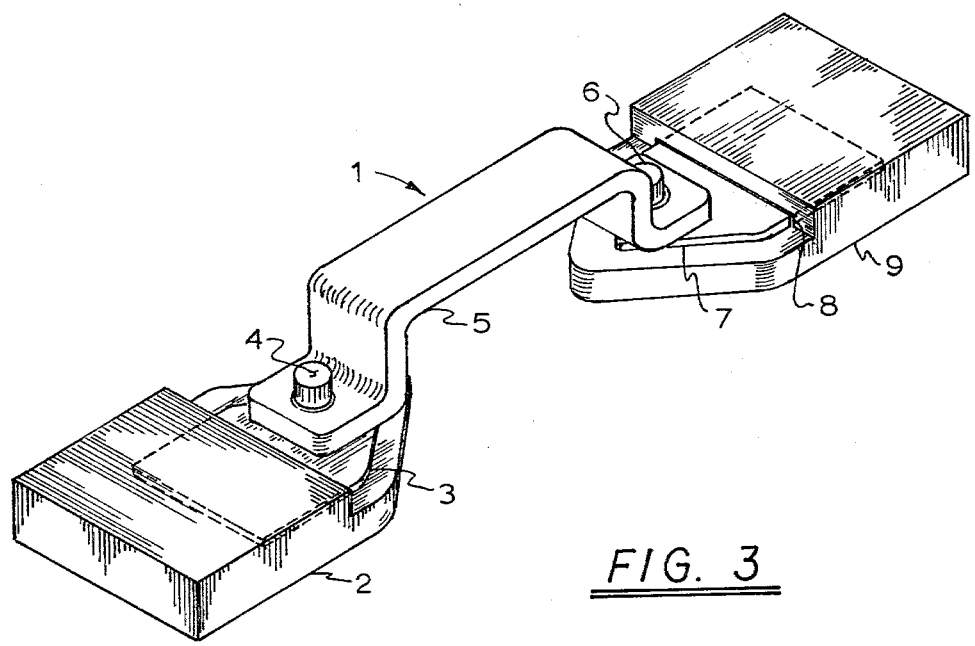
FIG. 3

KNEE STABILIZER

This is a continuation of application Ser. No. 919,870 filed June 28, 1978 now abandoned.

BACKGROUND OF THE INVENTION

This invention relates to an improved new assembly of knee stabilizer. More particularly, this invention relates to a new and improved double hinged single side brace for use in support and protection of a knee joint and to the medial collateral ligament of lateral collateral ligament of the knee.

The knee-joint is made up of two condyloid joints and a third joint, partly arthrodial, but not completely so, since the articular surfaces are not mutually adapted to each other, so that the movement is not a simple gliding one. The principal movements that take place at the knee-joint are flexion and extension. The movements of flexion and extension at this joint differ from those in a typical hinge joint, such as the elbow, in that the axis around which motion takes place is not a fixed one but shifts forward during extension, as a gliding movement is superposed on the rolling, and shifts backward during flexion.

Although the knee-joint has been described as a hinge joint, it is really of a much more complicated character. It must be regarded as consisting of three articulations, of two different kinds. The first kind is a condyloid articulation; in this form of joint, an ovoid articular surface, or condyle, is received into an elliptical cavity in such a manner as to permit flexion, extension, abduction, adduction, and circumduction, but no axial rotation. The second kind of articulation involved is arthtodial; this is a joint which permits only gliding movement. It is formed by the apposition of plane surfaces, or one slightly concave, the other slightly convex, the amount of motion between them being limited by the ligaments or osseous processes surrounding the articulation.

Persons who have sustained knee injuries, who have had operations to remove cartilage, or who have weak knee joints from causes, such as arthritis or atheletes who have sustained an injury to the medial collateral ligament or lateral collateral ligament of the knee, need protection principally against lateral motion of the knee, that is, motion may be the result, for example, of a blow to the side of the knee. At the same time, a suitable knee brace should not interfere with the normal flexion and extension of the leg. The brace should protect the knee against sidewise motions during both flexion and extension; this means that the bracing structure should continue to lie parallel to the parts of the leg above and below the knee joint in all postions of the brace structure should remain substantially at the knee and provide protection to the knee.

The knee joint has four principal ligaments, one on either side and two on the inside. There ligaments may be strained or torn in sports and accidents. Injuries to these ligaments can be serious and must be properly treated if disability is to be avoided. Above all, repeated injury or strains before healing must be avoided. All degrees of ligament injuries will lead to some atrophy of the quadriceps and hamstring muscle groups.

Many previous knee braces and protection devices have been simple hinged structures pivotable about a fixed point, which cannot move parallel to the complex motion of the knee joint. Some knee braces for support and protection of the knee joint comprises both an inner and outer bracing structures each a rigid planar and elongated arm and pivoted about a fixed point. The fixed point lies on and parallel to the knee and leg. During motion and a sideways blow the rigid planar arms may cause further injury or discomfort to the already injured ligaments of the knee joint.

Some of the previous knee braces fail to provide protection to the injured knee ligaments. While other braces may lie parallel to the leg and knee joint while it is extended, or the leg is flexed the bracing structure fails to follow the motion accurately.

SUMMARY OF THE INVENTION

Objects of the present invention are to provide for an improved knee stabilizer assembly which permits and provides freedom of movement of the knee during flexion and extension without restriction or physical discomfort during movement.

Another object of the present invention is to provide an improved knee stabilizer assembly which permits and provides for use on an already injured knee and provides prevention of further injury or strain.

Another object of the present invention is to provide a rigid double hinged single side knee brace pivotally hinged to padded upper and lower plates for easy securing and removal to the wearer's leg.

It is another object to provide such a knee brace stabilizer that does not interfere with normal extension and flexion of the wearer's leg, while preventing sidewise motion of the knee joint whether the leg is flexed or extended.

The knee stabilizer of the present invention includes a bracing structure comprising a rigid support bar substantially having a concave off-set through its center portion, and at one end pivotally hinged to an upper padded plate and at the other end pivotally hinged to a lower padded plate. The concave off-set of the rigid support is placed along side the knee joint opposite the injured ligament.

In preferred embodiments, the present invention encompasses a knee stabilizer for support and protection of a knee joint by a double hinged single side brace comprising a rigid support structure having a concave off-set through its center section. Upper securing means removably secures the padded plates to which the upper end of the rigid support structure is pivotally hinged to the wearer's upper leg above the knee joint for movement with the upper leg and limited motion parallel to the upper leg, and lower securing means removably secures the padded plate to which the lower end of the rigid support structure is pivotally hinged to the wearer's lower leg below the knee joint for movement with the lower leg and limited motion parallel to the lower leg. The support and stabilizing structure has a single rigid support bar having a concave off-set through its center portion and doubly hinged each at the upper and lower end of the rigid support bar. The movement of the leg by normal flexion and extension of the wearer's knee is freely permitted by the double hinged arrangement. The movement comprises any manner consistent with the double hinged action permitted by the rigid support bar and normal to the plane of the rigid support bar, thereby preventing sidewise motion of the knee joint.

Other objects, feature and advantages will appear from the following description of a preferred embodiment of the invention, taken together with the attached drawings, in which:

FIG. 1 shows the knee stabilizer according to the present invention in place with respect to the extended leg of the wearer;

FIG. 2 shows the knee stabilizer according to the present invention in relation to the flexed leg of the wearer;

FIG. 3 is a perspective view of the knee stabilizer and support according to the present invention.

Referring to the drawings, FIGS. 1–3, the knee stabilizer and support of the present invention includes a single rigid support bar 1 having a concave off-set 5 through the center portion of the support bar. The support bar has two end portions which are continuations of the support bar. Each end portion is provided with an opening which accommodates a means for pivotally fastening 4 and 6 the end portion of the support bar to plates 3 and 7. The plates 3 and 7 are pivotally fastened 4 and 6 to the end portion of the rigid support bar 1. Such pivotal connection is essential to the function of the knee stabilizer, as discussed in the following.

Each of the plates 3 and 7 are inserted integrally into slots 8 to be part of support pads 2 and 9. Each pad is provided of foam rubber or the like for comfortable wear. Referring to FIG. 1 and FIG. 2 the knee stabilizer is in place on the wearer's leg. The plates 3 and 7 inserted into the pads 2 and 9 are generally parallel to the upper and lower pants of the wearer's leg even at flexion or extension. The plates in the pads are removably fastened securely to the wearer's leg 10. Such fastening means 10 as an elastic cuff, two way stretch material, tape, straps and the like can be used.

The off-set center portion 5 of the knee stabilizer is purposefully designed to avoid pressure against the knee joint of the wearer. The pivotally mounted plates 3 and 7 and pads 2 and 9 are removably fastened securely to the wearer's leg, one pad to the upper part of the wearer's leg above the knee joint and one pad to the lower part of the wearer's leg below the knee joint. The three part construction with the double hinged action allows the stabilizer to translate the normal leg action of extension and flexion into conformed and supported bracing structure. The combination of motions permitted by the three part construction results in the motion of the pads and plates with respect to the rigid support bar that closely parallels the natural action of the knee joint. The rigid support bar 1 closely and accurately follows the action of the wearer's knee and at all times continuing to provide support and stability to the knee joint. Especially, provided and desirable is protection against sidewise forces.

The knee stabilizer is attachable to the inner or outer leg. Preferably the knee stabilizer is positioned and secured on the side of the knee opposite the ligament to be protected. The raised center portion of the rigid support bar is placed directly over the medial or lateral ligament.

By the double hinge arrangement the motions of flexion or extension are easily followed by the knee stabilizer with the accompanying support. The principle upon which the invention is based, as well as the operation of the double hinged arrangement, is best understood by referring to FIGS. 1 and 2. The bracing structure remains generally parallel to the knee joint, but the action of the joint formed by the stabilizer accurately parallels the action of the individual wearer's knee. At all times the knee stabilizer of this invention remains substantially displaced, but parallel and adjacent to the knee joint, continuing to provide protection against sidewise forces. Translational motion of the stabilizer is limited by the fastening means 10.

By using the present invention, it is thus possible to have a convenient, effective means for stabilizing and supporting the knee joint and thereby eliminate discomfort or possible injury or reinjury to the knee joint. The double hinge arrangement is a novel feature among knee braces. Also the off-set center portion of the rigid support bar of the knee stabilizer is novel in that it does not place pressure on the knee joint. Acting together, the off-set center and double hinge arrangement form the basis for an original and useful improvement in the design, function and operation of the present knee stabilizer.

Although a direct comparison between the present construction and other presently known conventional knee brace structures is difficult, it is the opinion of persons who have used the knee stabilizer that more than satisfactory results were obtained. For example, football players, who had each experienced stretched medial collateral ligaments of the knee, wore the described knee stabilizer in game conditions and practice. No reinjury of the knee occurred under those severe stress condition of use. Each player was able to perform his prescribed duties.

While certain novel features of the invention have been disclosed herein, and pointed out in the annexed claims, it will be understood that, in accordance with the doctrine of equivalents, various omissions, substitutions and changes may be made by those skilled in the art without departing from the spirit and scope of the invention.

What is claimed is:

1. A knee stabilizer for support and protection of a knee joint consisting of:
   (a) a rigid support bar having a raised center portion, an upper end and a lower end;
   (b) an upper padded plate non slidably pivotally hinged to said upper end of said support bar;
   (c) a lower padded plate pivotally hinged to said lower end of said support bar; and
   (d) upper securing means for removably securing said upper padded plate to the upper leg above the knee joint and lower securing means for removably securing said lower padded plate to the lower leg below the knee joint.

2. The knee stabilizer of claim 1 wherein said center portion of the rigid support bar is substantially concave off-set with respect to said upper end and said lower end of said support bar, whereby said rigid support bar is raised from the side of the knee joint.

3. The knee stabilizer of claims 1 and 2 wherein said upper securing means is an adjustable strap and said lower securing means is an adjustable strap.

4. A knee stabilizer for support and protection of a knee joint consisting of:
   (a) a rigid support bar having a raised center portion, an upper end and a lower end;
   (b) an upper padded plate pivotally non slidably hinged to said upper end of said support bar;
   (c) a lower padded plate pivotally hinged to said lower end of said support bar;
   (d) said knee stabilizer further including an elastic cuff adapted to be worn adjacent the knee joint;
   (e) said upper padded plate and said lower padded plate inserted into pockets secured to said elastic cuff and retaining said upper end and said lower end of the rigid support bar.

5. The knee stabilizer of claim 4 wherein said center portion of the rigid support bar is substantially concave off-set with respect to said upper end and said lower end of said support bar, whereby said rigid support bar is raised from the side of the knee joint.

6. Method of supporting and protecting a knee joint primarily the ligaments associated therewith by positioning and securing on the side of the knee on the side opposite the ligament to be protected the knee stabilizer of claim 1.

7. Method of supporting and protecting a knee joint primarily the ligaments associated therewith by positioning and securing on the side of the knee on the side opposite the ligament to be protected the knee stabilizer of claim 1 with the raised center portion directly over the medial or lateral ligament.

* * * * *

UNITED STATES PATENT AND TRADEMARK OFFICE
CERTIFICATE OF CORRECTION

PATENT NO. : 4,249,524

DATED : February 10, 1981

INVENTOR(S) : George C. Anderson

It is certified that error appears in the above-identified patent and that said Letters Patent is hereby corrected as shown below:

Col. 4, claim 3, line 1, the "and" in the phrase "claims 1 and 2" is replaced with an --or-- so that the phrase reads --claims 1 or 2--.

Signed and Sealed this

Third Day of February, 1987

Attest:

DONALD J. QUIGG

Attesting Officer

Commissioner of Patents and Trademarks